United States Patent
Mattson et al.

(10) Patent No.: US 7,564,940 B2
(45) Date of Patent: Jul. 21, 2009

(54) RADIATION MASK FOR TWO DIMENSIONAL CT DETECTOR

(75) Inventors: Rodney A. Mattson, Mentor, OH (US); William C. Brunnett, Jacksonville, FL (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 217 days.

(21) Appl. No.: 10/565,291

(22) PCT Filed: Jul. 15, 2004

(86) PCT No.: PCT/IB2004/002352

§ 371 (c)(1),
(2), (4) Date: Jan. 20, 2006

(87) PCT Pub. No.: WO2005/006986

PCT Pub. Date: Jan. 27, 2005

(65) Prior Publication Data

US 2006/0227930 A1 Oct. 12, 2006

Related U.S. Application Data

(60) Provisional application No. 60/489,130, filed on Jul. 22, 2003.

(51) Int. Cl.
*H05G 1/64* (2006.01)
*G21K 1/10* (2006.01)

(52) U.S. Cl. .................. 378/19; 378/98.8; 378/154; 250/370.09

(58) Field of Classification Search .............. 378/19, 378/98.8, 147, 149, 154; 250/370.09
See application file for complete search history.

(56) References Cited

U.S. PATENT DOCUMENTS

| | | | | |
|---|---|---|---|---|
| 5,487,098 | A | | 1/1996 | Dobbs .................. 378/19 |
| 5,635,718 | A | * | 6/1997 | DePuydt et al. ........ 250/370.09 |
| 5,668,851 | A | | 9/1997 | Dobbs .................. 378/19 |
| 5,799,057 | A | * | 8/1998 | Hoffman et al. ........ 378/147 |
| 5,949,850 | A | * | 9/1999 | Tang .................. 378/154 |
| 5,991,357 | A | | 11/1999 | Marcovici et al. ........ 378/19 |
| 5,991,537 | A | | 11/1999 | McKeon et al. ......... 395/704 |
| 6,181,767 | B1 | | 1/2001 | Harootian ............ 378/19 |
| 6,298,113 | B1 | | 10/2001 | Duclos et al. .......... 378/19 |
| 6,304,626 | B1 | | 10/2001 | Adachi et al. ......... 378/19 |
| 6,396,898 | B1 | * | 5/2002 | Saito et al. ........... 378/19 |
| 6,426,991 | B1 | * | 7/2002 | Mattson et al. ........ 378/19 |
| 6,587,538 | B2 | * | 7/2003 | Igarashi et al. ........ 378/19 |

(Continued)

FOREIGN PATENT DOCUMENTS

WO WO 2004/027785 A1 4/2004

*Primary Examiner*—Allen C. Ho

(57) ABSTRACT

A radiation detector for a computed tomography scanner includes a plurality of radiation detector modules. Each detector module includes an anti-scatter module, at least one radiation absorbing mask and a detector subassembly module. The anti-scatter module includes radiation absorbing anti-scatter plates. The detector subassembly module includes a substrate and an array of detector elements. The radiation absorbing mask is a photoetched grid, formed of a radiation absorbing material and is positioned between the anti-scatter module and the detector elements of array. The strip of the grid, that is parallel to the anti-scatter plates, is wider than each anti-scatter plate. The detector module is aligned with a spatial focus by inserting the alignment pins into the alignment openings of the radiation absorbing mask and the alignment openings of the detector subassembly module.

23 Claims, 12 Drawing Sheets

U.S. PATENT DOCUMENTS

| | | | |
|---|---|---|---|
| 6,778,637 B2 * | 8/2004 | Luhta et al. ................. 378/154 |
| 6,917,664 B2 * | 7/2005 | Chappo et al. ................ 378/19 |
| 6,934,354 B2 * | 8/2005 | Hoffman ..................... 378/19 |
| 6,951,628 B2 * | 10/2005 | Eidam et al. ................ 264/401 |
| 6,982,423 B2 * | 1/2006 | Elgali .................... 250/370.11 |
| 7,145,986 B2 * | 12/2006 | Wear et al. ................. 378/98.8 |
| 7,177,387 B2 * | 2/2007 | Yasunaga et al. .............. 378/19 |
| 7,190,759 B2 * | 3/2007 | Ratzmann .................... 378/19 |
| 7,202,482 B2 * | 4/2007 | Yokoi et al. ............ 250/370.09 |
| 7,233,640 B2 * | 6/2007 | Ikhlef et al. ................... 378/19 |
| 7,259,376 B2 * | 8/2007 | Pohan .................. 250/370.09 |
| 7,339,176 B2 * | 3/2008 | El-Hanany et al. ..... 250/370.09 |
| 2001/0002699 A1 | 6/2001 | Such et al. .................. 250/367 |
| 2002/0003863 A1 | 1/2002 | Ohkoda ..................... 378/154 |
| 2002/0150215 A1 | 10/2002 | Barnes et al. ............... 378/197 |
| 2002/0168052 A1 | 11/2002 | Castleberry ................ 378/154 |
| 2003/0021379 A1 | 1/2003 | Klotz et al. ................. 378/154 |
| 2006/0118730 A1 * | 6/2006 | Hefetz et al. ........... 250/370.09 |
| 2006/0198493 A1 * | 9/2006 | Pohan et al. ................. 378/19 |

* cited by examiner

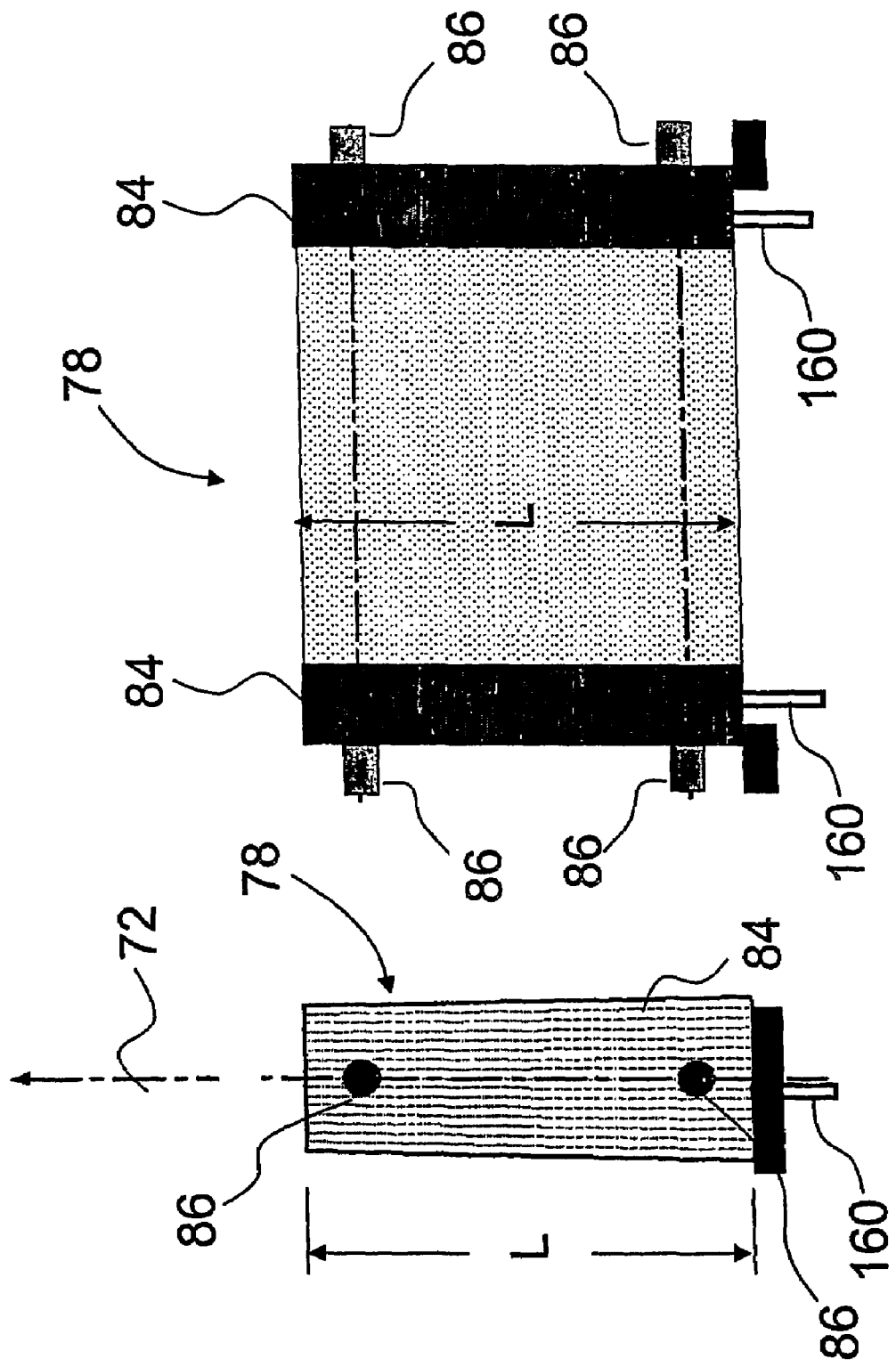

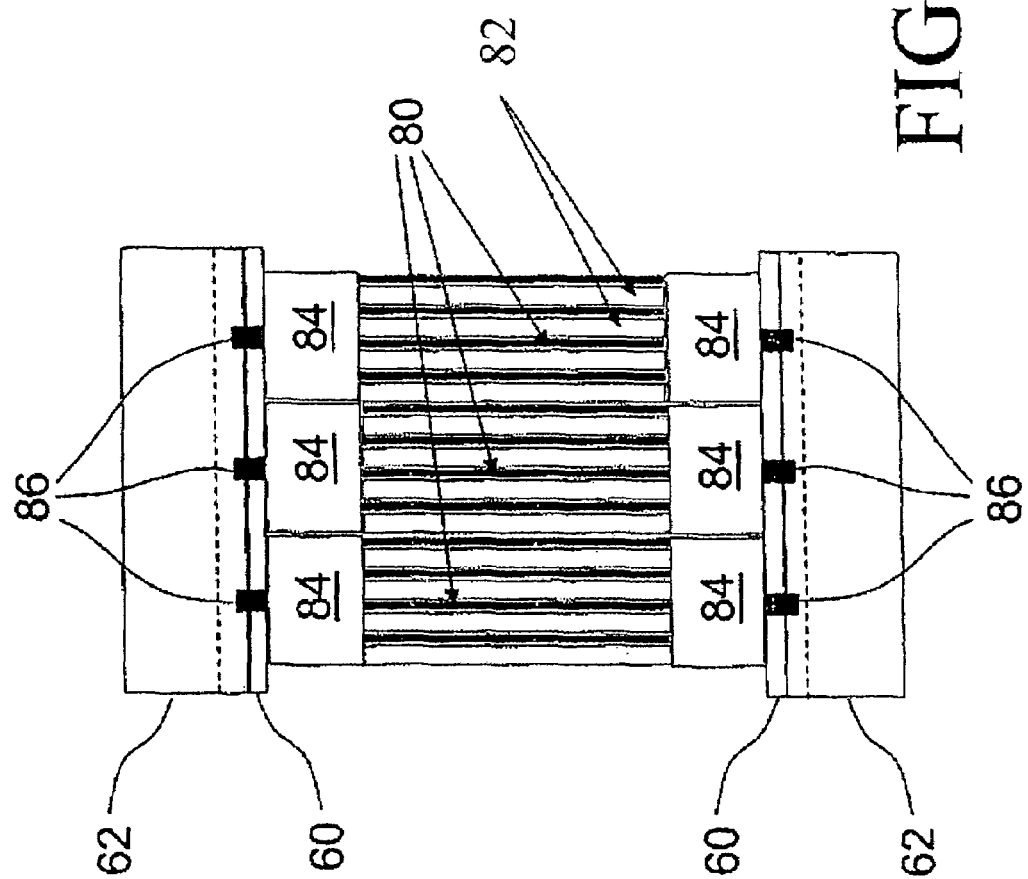

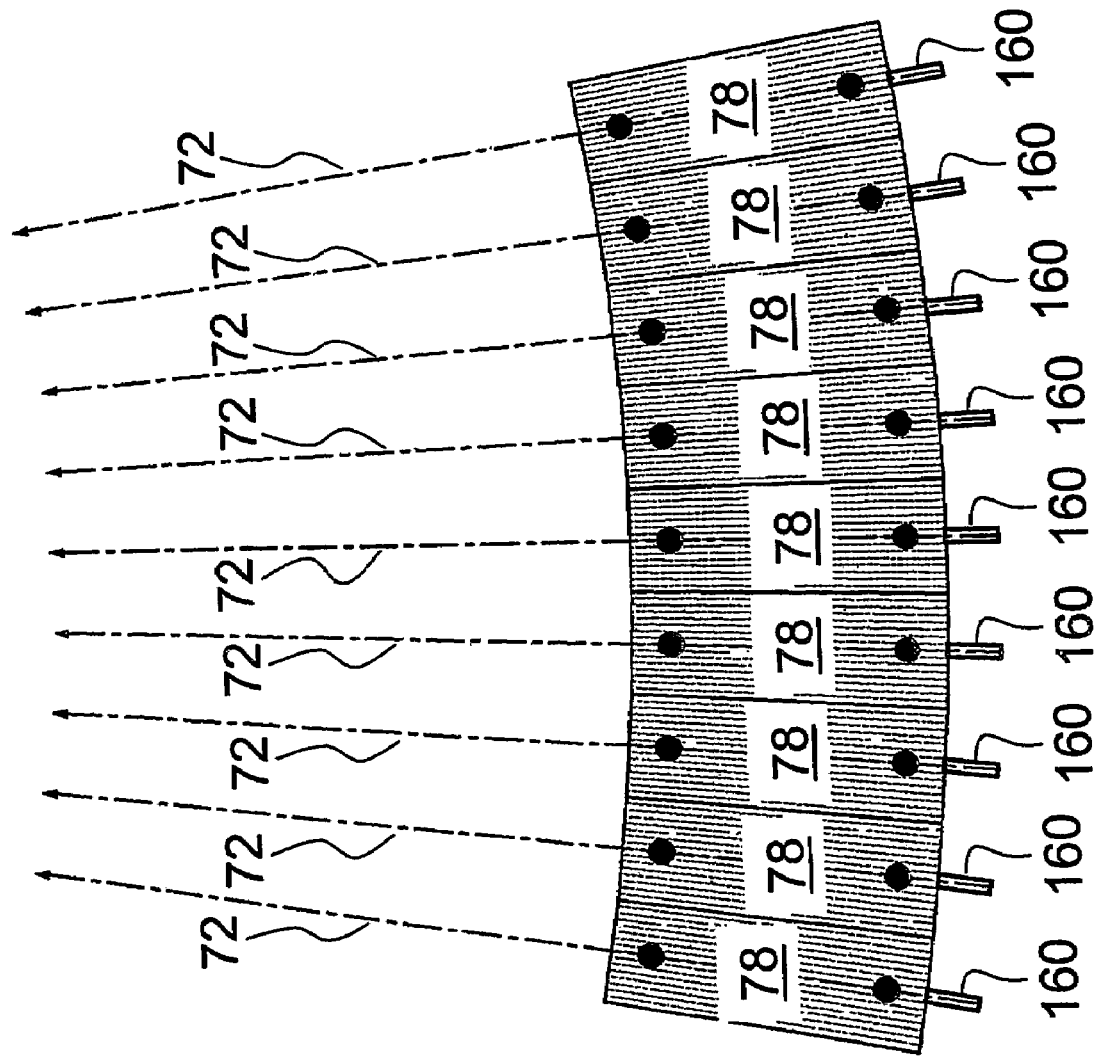

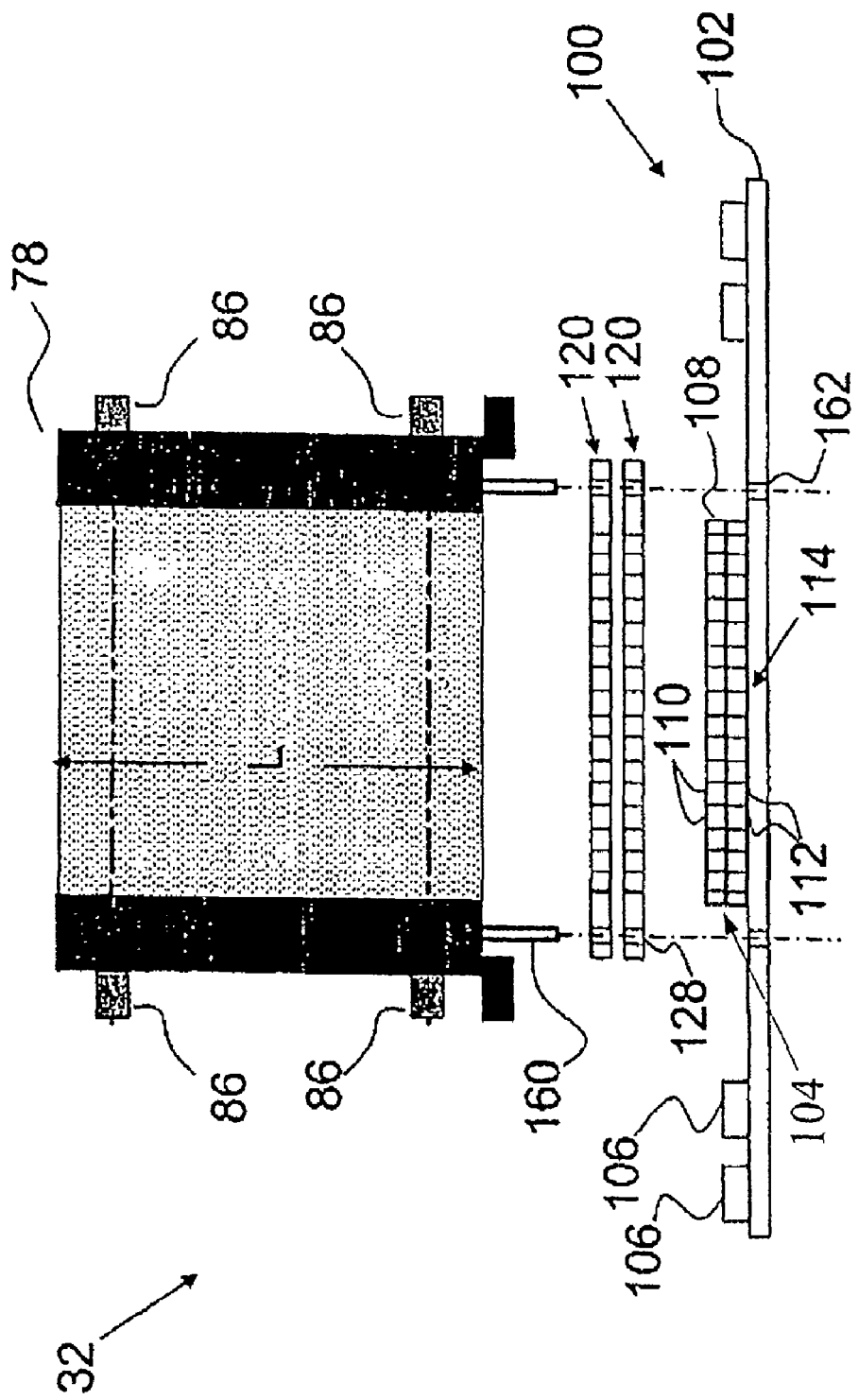

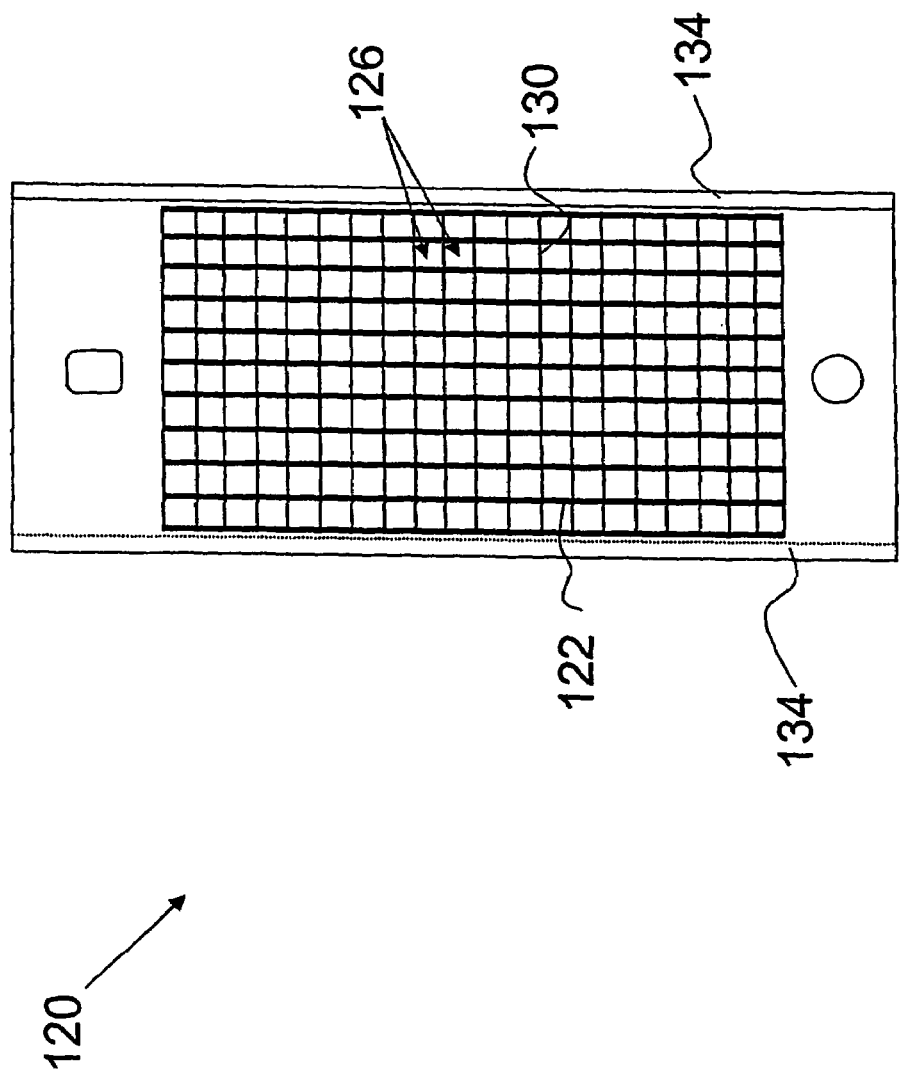

RADIATION MASK FOR TWO DIMENSIONAL CT DETECTOR

CROSS REFERENCE TO RELATED APPLICATIONS

This application claims the benefit of U.S. provisional application Ser. No. 60/489,130 filed Jul. 22, 2003, which is incorporated herein by reference.

The present invention relates to the diagnostic imaging arts. It particularly relates to computed tomography scanners with a two-dimensional detector arrays, and will be described with particular reference thereto. However, the invention will also find application with other two-dimensional radiation detectors for a variety of imaging and non-imaging applications employing x-rays, radiation from an administered radiopharmaceutical, light, or other types of radiation.

Computed tomography (CT) imaging typically employs an x-ray source that generates a fan-beam, wedge-beam, or cone-beam of x-rays that traverse an examination region. A subject arranged in the examination region interacts with and absorbs a portion of the traversing x-rays. A one- or two-dimensional radiation detector including an array of detector elements is arranged opposite the x-ray source to detect and measure intensities of the transmitted x-rays.

Typically, the x-ray source and the radiation detector are mounted at opposite sides of a rotating gantry such that the gantry is rotated to obtain an angular range of projection views of the subject. The projection views are reconstructed using filtered backprojection or another reconstruction method to produce a three-dimensional image representation of the subject or of a selected portion thereof. Typically, the reconstruction assumes that the radiation traversed a linear path from the x-ray source directly to the detector. Any scattered radiation that reaches the detector degrades the resultant image.

The radiation detector typically includes scintillator crystal arrays, each crystal of which produces bursts of light, called scintillation events, in response to x-rays. Arrays of photodetectors, such as monolithic silicon photodiode arrays, are arranged to view the scintillator crystal arrays and produce analog electrical signals indicative of the spatial location and intensity of the scintillation event.

Typically, the detector is focus-centered structure, in which a plurality of scintillator crystal arrays defines a curved detection surface defining a focus that coincides with a focal spot of the x-ray beam. Anti-scatter elements, such as arrays of anti-scatter plates, are mounted in front of the scintillator array, and are precisely aligned with the focus to admit unscattered x-rays and block scattered x-rays, which would otherwise contribute to the measurement as noise. In present anti-scatter elements, plates with heights of between one centimeter and four centimeters are typical. The spacing between the anti-scattering plates defines slits, through which the direct or non-scattered x-rays pass unimpeded. However, scattered x-rays are angularly deviated due to the scattering and strike the anti-scatter plates which absorb the scattered x-rays before they reach the scintillator crystal array.

A conventional detector board is assembled starting with a monolithic photodiode array, which is mounted to ceramic support substrates for rigidity. The scintillator crystal arrays are bonded to the monolithic photodiode arrays. Anti-scatter elements are next mounted and aligned with the interface between adjacent scintillation crystals on the detector boards. The detector boards with joined anti-scatter elements are mounted onto a mechanical base plate or support and manually aligned with the focal spot of the x-ray beam. Typically, a test projection image is made and examined to determine which anti-scatter grids are misaligned. The detector boards are shimmed or the anti-scatter elements re-aligned with the detector array. The test image and the adjustment routine are repeated until satisfactory test images are obtained.

A common problem in such detector arrays is cumulative alignment or stack-up errors. Typically, the anti-scatter plates are several centimeters long. The thickness of these plates is comparable with the inter-gap spacing between the scintillation crystals and spacing is comparable with the crystals size, e.g., of about 0.5-3.0 mm. The large anti-scatter plates require precise alignment of the anti-scatter elements with the spatial focal point. As detector arrays get larger, e.g., 32 rows of detectors, 64 rows of detectors, etc., it becomes progressively more difficult to maintain every anti-scatter plate accurately positioned between the scintillation crystals over their entire length. Slight misalignment, deflection along the plate's length, or wobble of a plate due to vibration or rotation, can cause the plate to shadow the adjoining scintillation crystals. Shadowing, in turn, leads to reduced x-ray intensities, which signify more dense material along the x-ray path. This leads to image artifacts, which generally manifest as rings in the image reconstruction. Spatially non-uniform shadowing also leads to spectral differences in the detected x-rays and non-linear detector array characteristics.

Further, the replacement of defective detector electronics requires removal of the entire detector module including anti-scatter grid. When the new parts are installed the alignment process is repeated, making a field replacement of the defective detector expensive and time-consuming.

The present invention contemplates an improved apparatus and method that overcomes the aforementioned limitations and others.

According to one aspect of the invention, a two-dimensional radiation detector for a radiographic scanner is disclosed. A first aligning means aligns an anti-scatter module, disposed on a support frame, with a spatial focus. A second aligning means aligns the anti-scatter module with a detector subassembly module and a radiation absorbing mask. Each radiation subassembly module includes a substrate and an array of detector elements arranged on a substrate to detect radiation. The radiation absorbing mask is formed as a grid and arranged between the array of detector elements and the anti-scatter module.

According to another aspect of the invention, a computed tomography scanner is disclosed. An x-ray source is mounted to rotate about an examination region. The x-ray source emits a cone shaped x-ray beam from a radiation focal point that traverses the examination region. A two-dimensional radiation detector receives the cone beam of radiation that has traversed the examination region. The radiation detector includes a plurality of detector modules. Each detector module includes an anti-scatter module, a detector subassembly module, and a radiation absorbing mask that are aligned with each other. Each detector subassembly module includes a substrate and an array of detector elements arranged on the substrate to detect radiation. The radiation absorbing mask is positioned between the anti-scatter module and the detector elements. A reconstruction processor reconstructs signals from the detector elements into a volumetric image.

According to yet another aspect of the invention, a method is provided for manufacturing a radiation detector for a computed tomography scanner. An anti-scatter module is aligned with a detector subassembly module and a radiation absorbing mask. The anti-scatter modules are disposed on a support frame. The detector subassembly module includes a substrate and an array of detector elements arranged on the substrate to detect radiation. The radiation absorbing mask is disposed between the anti-scatter module and the array of the detector elements.

One advantage of the present invention resides in the improved uniformity in x-ray sensitivity among the individual scintillation crystals. The scintillation crystals are generally larger than the openings in the radiation absorbing mask, hence the spatial resolution of the detector is established by the radiation absorbing mask.

Another advantage of the present invention resides in a simplified process for assembling a detector module for computed tomography imaging.

Numerous additional advantages and benefits of the present invention will become apparent to those of ordinary skill in the art upon reading the following detailed description of the preferred embodiment.

The invention may take form in various components and arrangements of components, and in various steps and arrangements of steps. The drawings are only for the purpose of illustrating preferred embodiments and are not to be construed as limiting the invention.

FIG. 1 shows an exemplary computed tomography imaging apparatus employing a radiation detector assembly constructed in accordance with one embodiment of the invention.

FIG. 2 schematically shows a side view of an exemplary alignment plate according to an embodiment of the invention, with radial lines showing alignment relationships between alignment opening pairs and a spatial focal point of the radiation detector.

FIG. 3 shows an end view of a first embodiment of an anti-scatter element or module of the radiation detector of FIG. 1.

FIG. 4 shows a front view of the anti-scatter element or module of FIG. 5A.

FIG. 5 shows three anti-scatter modules of the type shown in FIGS. 3A-B mounted in the radiation detector array of FIG. 1.

FIG. 6 schematically shows several anti-scatter elements of the type shown in FIGS. 3-5 with radial lines shown that connect alignment protrusions of the anti-scatter modules with the spatial focal point of the radiation detector.

FIG. 7 shows an expanded side sectional of the detector module.

Figure 8:
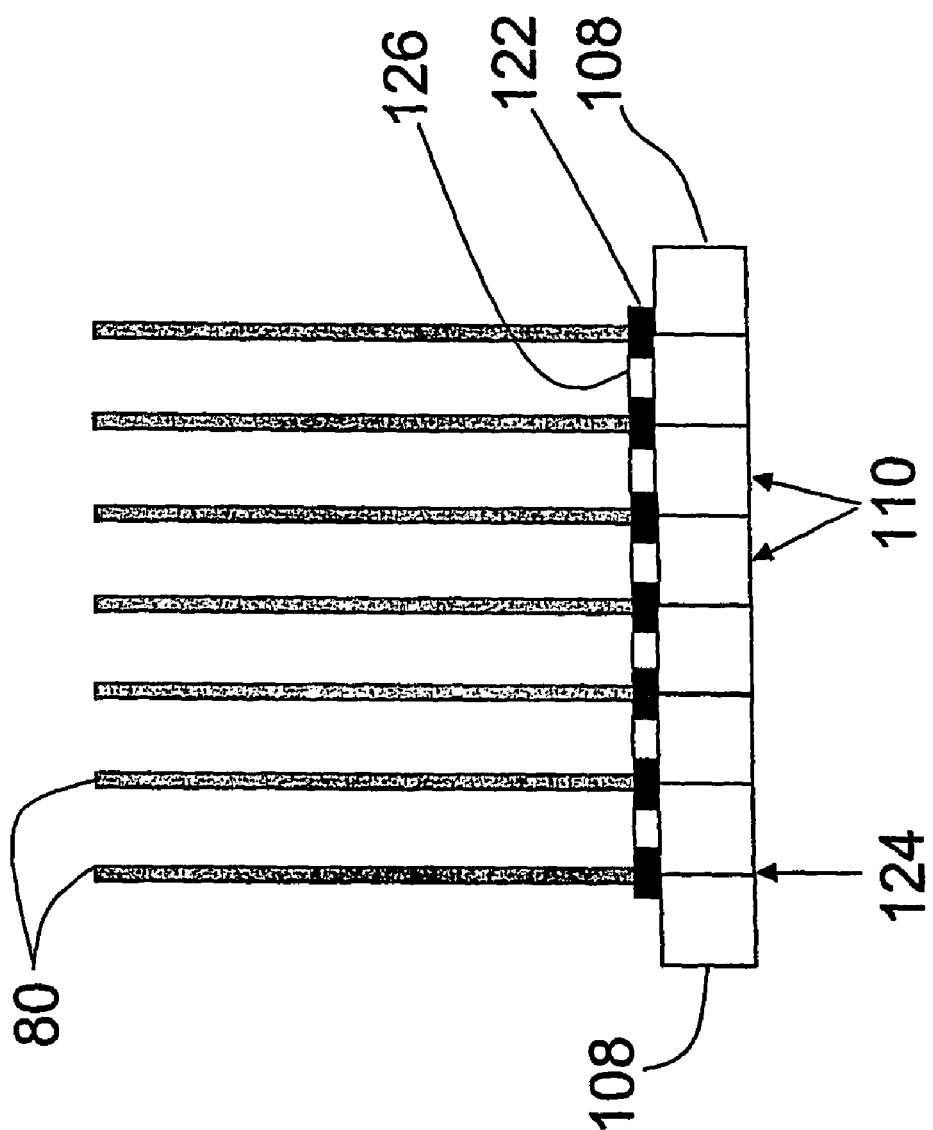

FIG. 8 shows a detailed side sectional view of the assembly.

Figure 9:
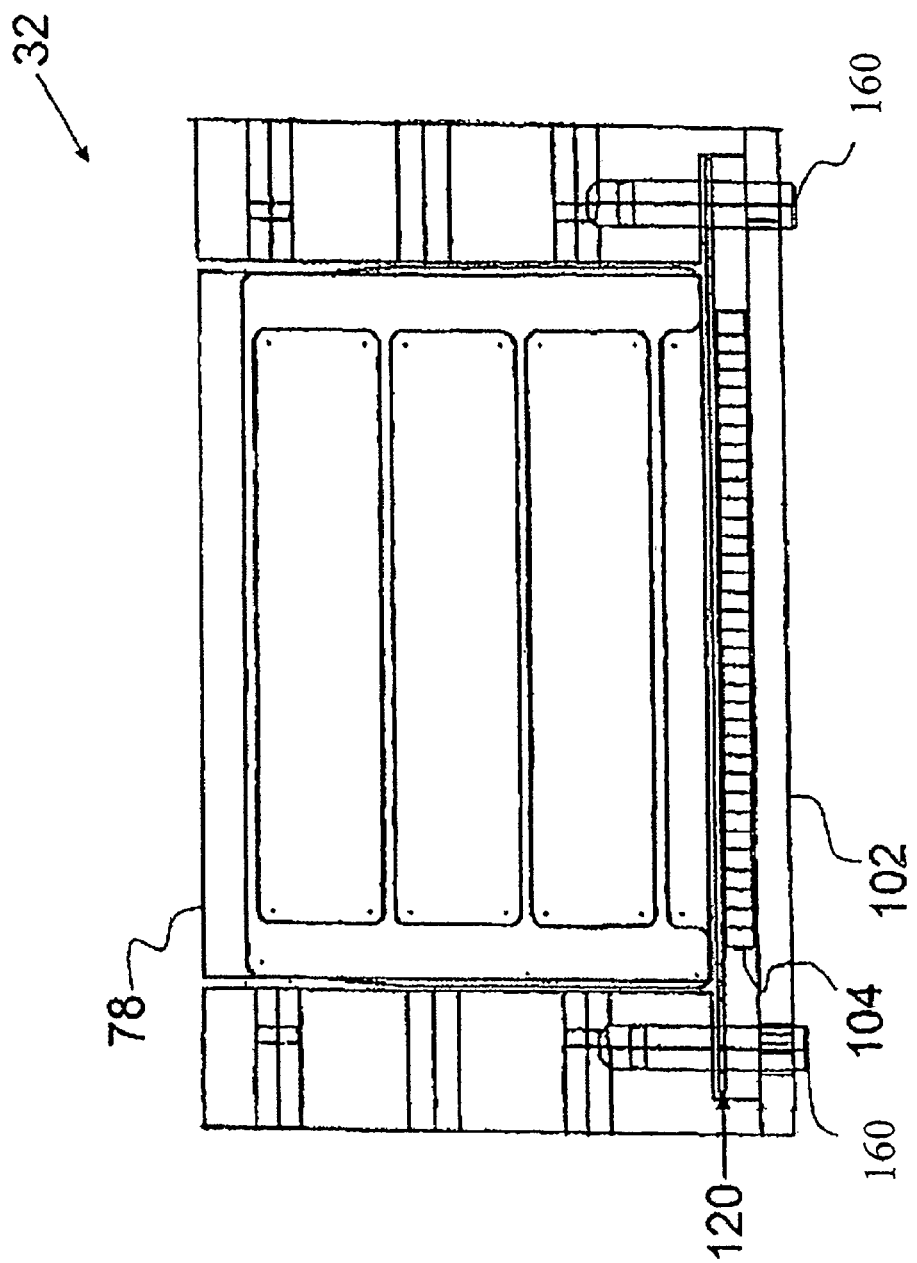

FIG. 9 shows a side view of the assembly.

FIG. 10A shows the radiation absorbing mask in detail.

FIG. 10B shows the interleaving of adjoining masks.

Figure 11:
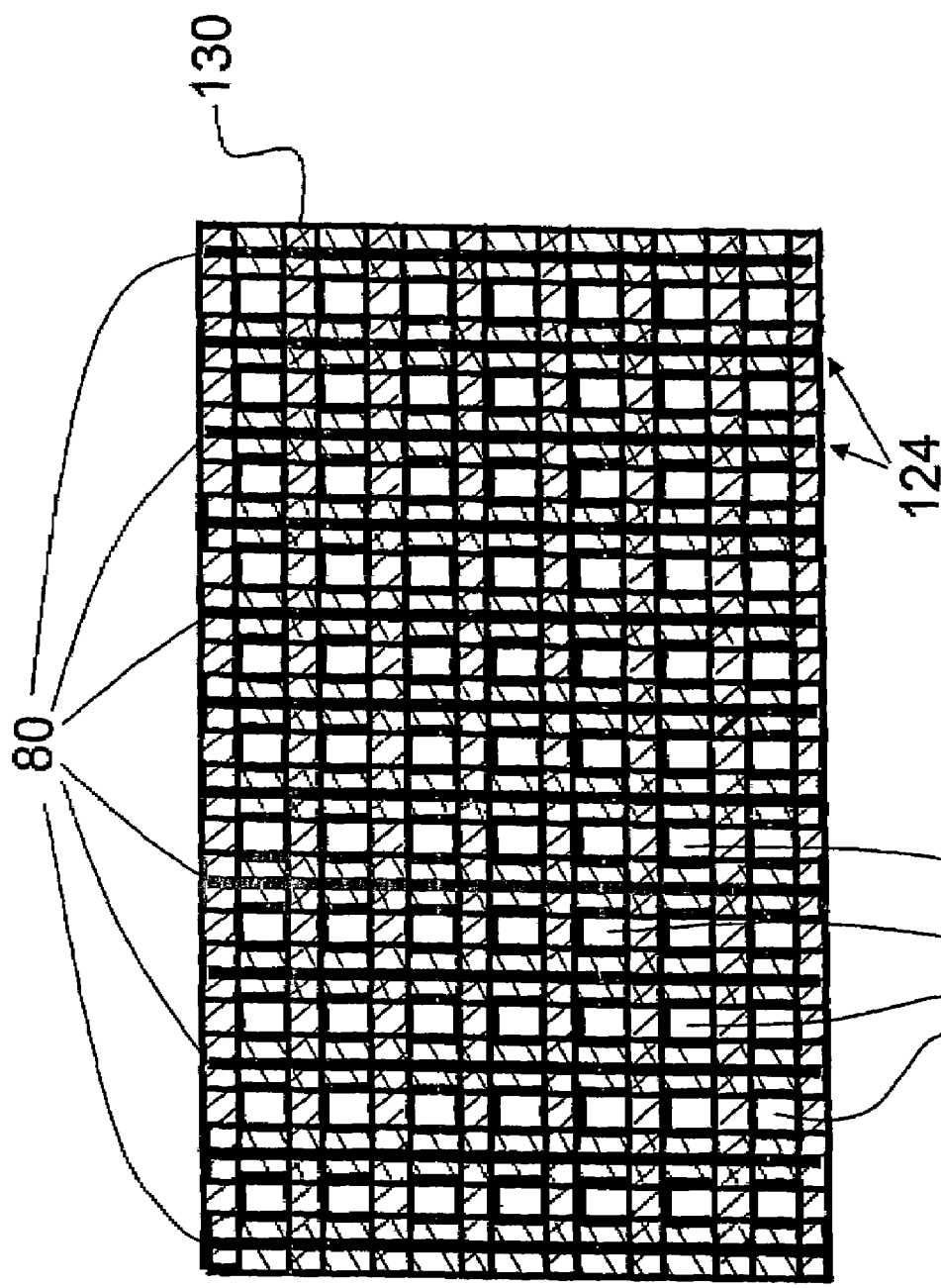

FIG. 11 schematically shows alignment of the detector elements of the detector module of FIG. 7 between anti-scatter plates of the anti-scatter module.

Figure 12:
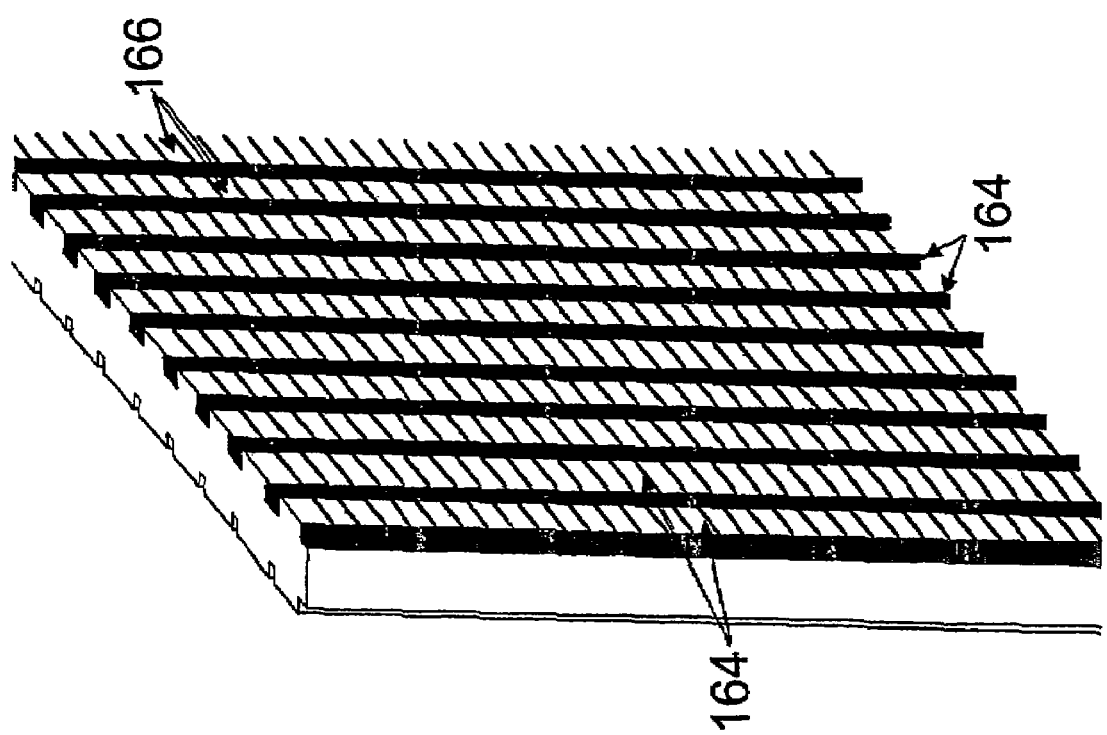

FIG. 12 shows the radiation absorbing mask.

Figure 1:
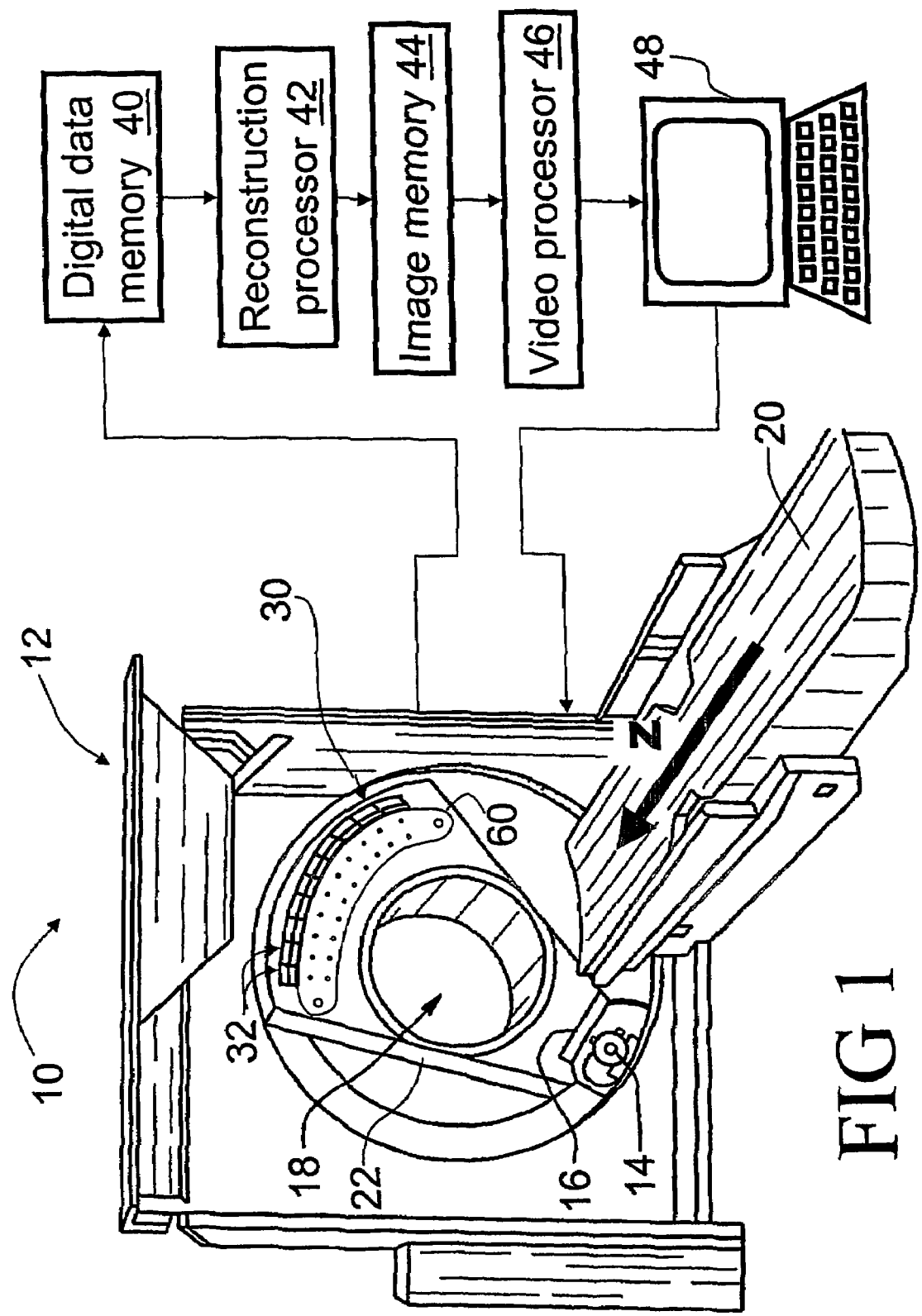
Figure 13:
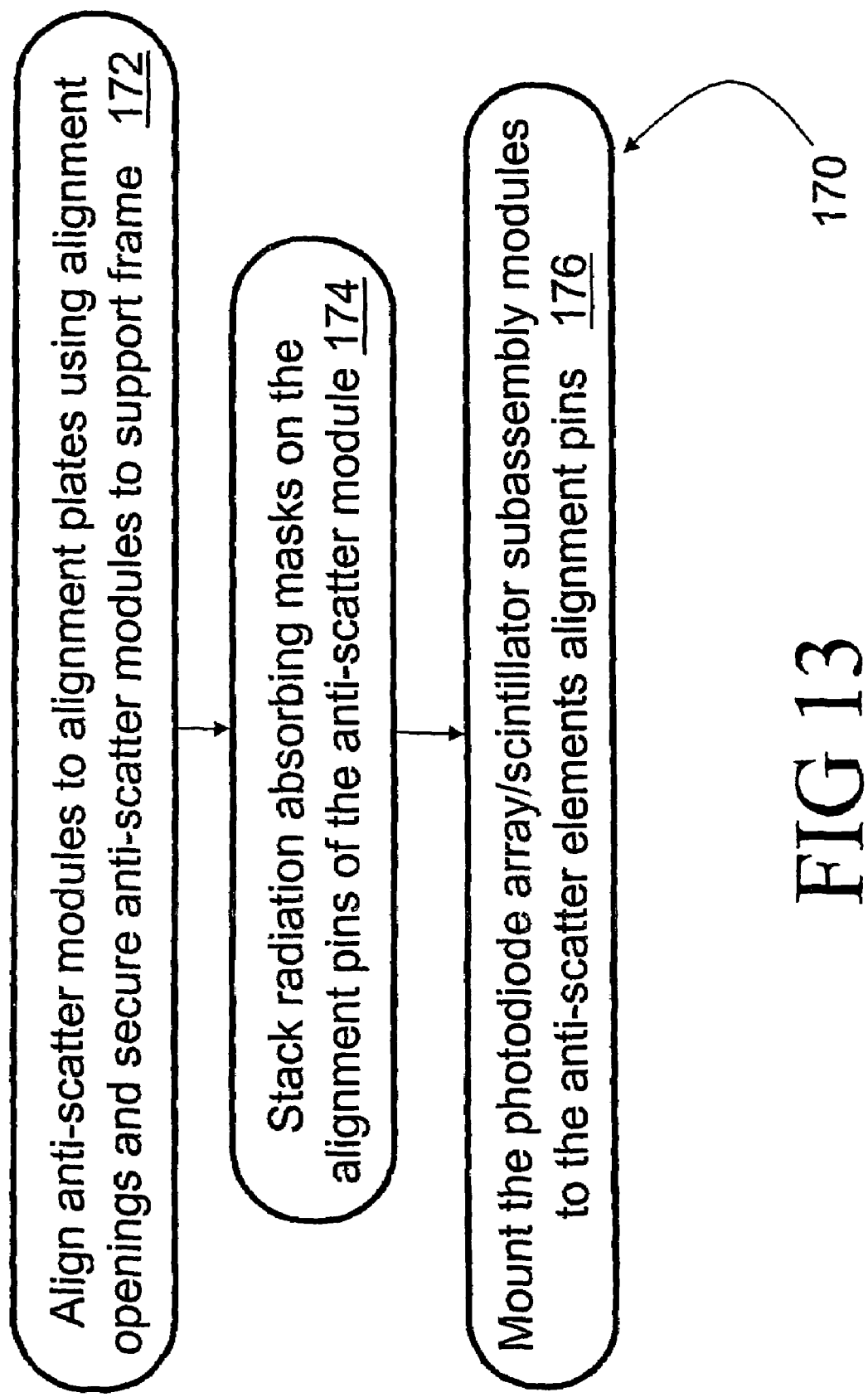

FIG. 13 illustrates a preferred method for assembling and mounting the radiation detector shown in FIG. 1.

With reference to FIG. 1, a computed tomography (CT) imaging apparatus or CT scanner 10 includes a stationery gantry 12. An x-ray source 14 and a source collimator 16 cooperate to produce a fan-shaped, cone-shaped, wedge-shaped, or otherwise-shaped x-ray beam directed into an examination region 18 which contains a subject (not shown) such as a patient arranged on a subject support 20. The subject support 20 is linearly movable in a Z-direction while the x-ray source 14 on a rotating gantry 22 rotates around the Z-axis.

In an exemplary helical imaging mode, the rotating gantry 22 rotates simultaneously with linear advancement of the subject support 20 to produce a generally helical trajectory of the x-ray source 14 and collimator 16 about the examination region 18. However, other imaging modes can also be employed, such as a multi-slice imaging mode in which the gantry 22 rotates as the subject support 20 remains stationary to produce a generally circular trajectory of the x-ray source 14 over which transverse parallel slice images are acquired. After the parallel slice images are acquired, the subject support 20 optionally steps a pre-determined distance in the Z-direction and the image acquisition is repeated to acquire a larger volumetric data set in discrete steps along the Z-direction.

A radiation detector assembly 30 is arranged on the gantry 22 across from the x-ray source 14. In the exemplary CT scanner 10, the radiation detector assembly 30 spans a selected angular range that preferably comports with a fan angle of the x-ray beam. The radiation detector assembly 30 includes a plurality of modules 32 for acquiring imaging data along a portion of the Z-direction in each projection view. The radiation detector assembly 30 is arranged on the rotating gantry 22 opposite to the x-ray source 14 and rotates therewith so that the radiation detector assembly 30 receives x-rays that traverse the examination region 18 as the gantry 22 rotates.

With continuing reference to FIG. 1, the rotating gantry 22 and the subject support 20 cooperate to obtain selected projection views of the subject along a helical trajectory or other trajectory of the x-ray source 14 relative to the subject. The path of the x-ray source 14 preferably provides sufficient angular coverage for each voxel of the imaged region of interest to prevent undersampling. Projection data collected by the radiation detector assembly 30 are communicated to a digital data memory buffer 40 for storage.

A reconstruction processor 42 reconstructs the acquired projection data, using filtered backprojection, an n-PI reconstruction method, or other reconstruction method, to generate a three-dimensional image representation of the subject or of a selected portion thereof which is stored in a volumetric image memory 44. The image representation is rendered or otherwise manipulated by a video processor 46 to produce a human-viewable image that is displayed on a graphical user interface 48 or another display device, printing device, or the like for viewing by an operator.

Preferably, the graphical user interface 48 is programmed to interface a human operator with the CT scanner 10 to allow the operator to initialize, execute, and control CT imaging sessions. The graphical user interface 48 is optionally interfaced with a communication network such as a hospital or clinic information network via which image reconstructions are transmitted to medical personnel, a patient information database is accessed, or the like.

Figure 2:
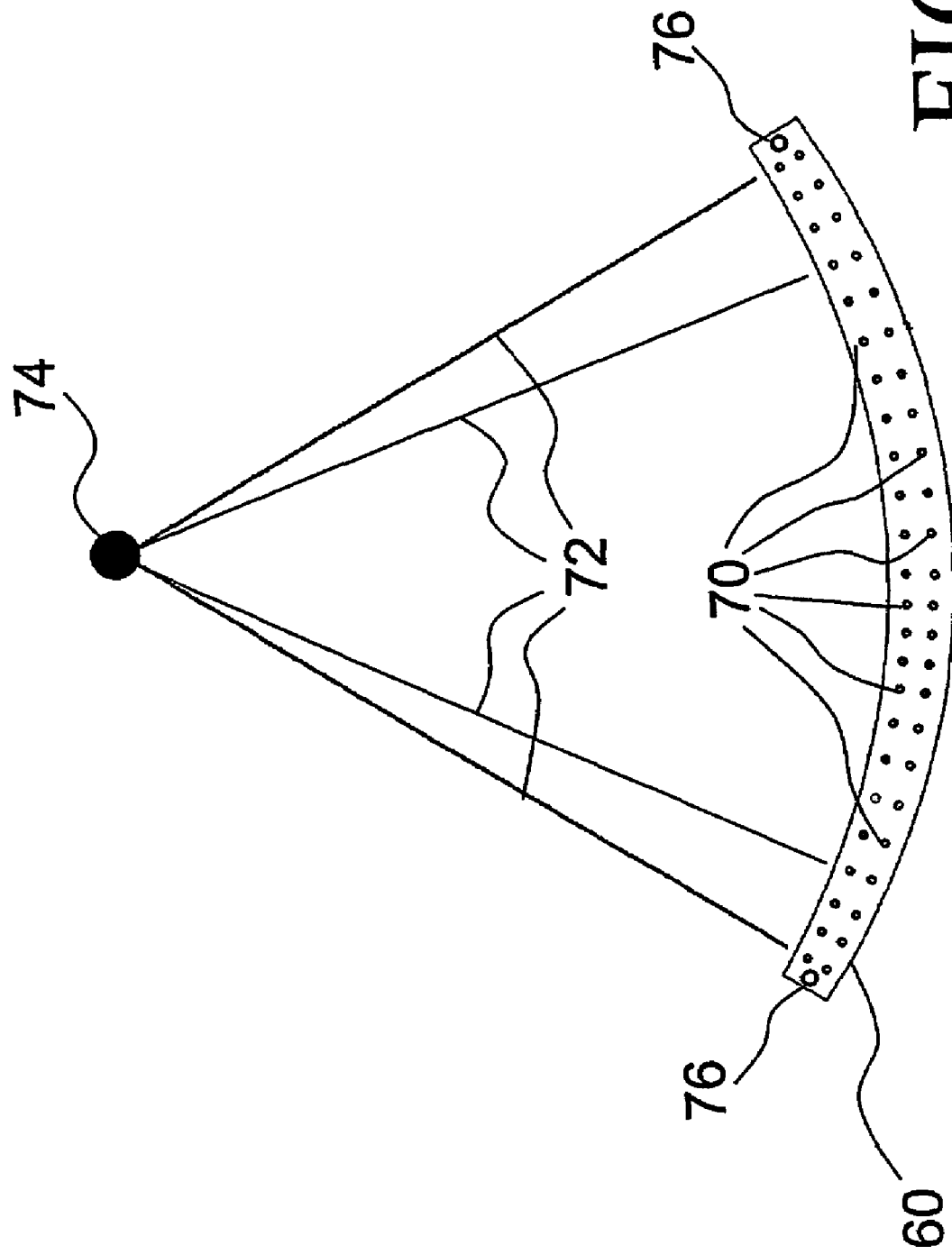

With continuing reference to FIG. 1 and with further reference to FIGS. 2 and 5, the radiation detector assembly includes a pair of alignment plates 60, positioned about support frame 62. A plurality of alignment openings 70 disposed on the alignment plates 60 for mounting and aligning of the detector modules 32. As shown in FIG. 2, the alignment openings 70 are arranged in pairs along radial lines 72 that converge at a spatial focal spot 74, which coincides with the focal spot of the x-ray source 14. In FIG. 2, a few exemplary radial lines 72 are shown to indicate the alignment of pairs of the alignment openings 70 with the spatial focal point 74. Further additional alignment openings 76 in the alignment plates 60 are included for mounting the plates 60 in the CT scanner 10.

With reference to FIGS. 3-5, each detector module 32 has an anti-scatter module 78, each including a plurality of anti-scatter plates or vanes 80 arranged generally in conformity with the rays or planes 72 and separated by radio translucent spacer plates 82. The spacer plates 82 taper to define a selected spacing and convergence angle between anti-scatter plates 80. The non-scattered radiation is directed parallel to the anti-scatter plates 80 and pass between any two of them, while scattered radiation angularly deviates from parallel with the anti-scatter plates 80 and is typically absorbed by the anti-scatter plates 80.

Although the anti-scatter plates or vanes 80 are generally parallel to one another, those skilled in the art will recognize that precisely parallel plates do not exactly align with the spatial focal point 74. That is, precisely parallel planes do not contain any points in common, and hence cannot contain the spatial focal point 74 in common. Preferably, the generally parallel anti-scatter plates or vanes 80 are each aligned with a plane 72 that intersects the spatial focal point 74. Such planes are close to, but not exactly, parallel over a length L of the anti-scatter plate 80 since L is short, compared a distance between the anti-scatter module 78 and the spatial focal point 74.

The anti-scatter plates or vanes 80 are preferably formed of a material with a high atomic number that is highly absorbing for radiation produced by the x-ray source 14, such as tantalum, tungsten, lead, or the like. The spacer plates 82 are formed of a material that is substantially translucent to radiation produced by the x-ray source 14, and are suitably formed of a plastic material. In a preferred embodiment, the spacer plates 82 are substantially hollow molded plastic frames, rather than full molded plastic slabs, to further reduce radiation absorption in the spacer plates 82.

The arrangement of generally parallel anti-scatter plates 80 and spacer plates 82 is secured at the sides by two end caps 84. Each end cap 84 includes alignment pins or other alignment protrusions 86 that are received in openings 70 to align the plates with the radial lines or planes 72, as best seen in FIG. 6.

With reference to FIG. 7, each detector subassembly module 100 includes a substrate 102, such as a circuit board, on which a detector array 104 and associated electronics 106 are mounted. In the preferred embodiment, the detector array 104 includes a scintillator crystal array 108 including individual scintillation crystals 110, each optically coupled to a photodetector 112 of a photodetector array 114. The scintillator crystal array 108 converts x-rays to light that is detectable by the photodetector array 114. The photodetector array 114 is preferably a monolithic array of silicon photodiodes, amorphous silicon, charge-coupled devices, or other semiconductor photodetectors. Other detector arrays such as CZT detectors that convert x-rays directly into electrical signals are also contemplated.

With continuing reference to FIG. 7 and further reference to FIGS. 8, 9 and 10A, an x-ray radiation absorbing mask 120 is arranged between the base of each anti-scatter module 78 and the scintillator crystal array 108. The radiation absorbing mask 120 has the form of a grid and surrounds a periphery of the radiation receiving face of each of the scintillation crystals 110. A width of a Z-direction grid strip 122 of the radiation absorbing mask 120, which is mounted parallel to the anti-scatter plates 80 is wider than the width of one anti-scatter plate 80 and equal to or greater than a width of an intra-element gap 124 between detector elements. The Z-direction strips 122 of the radiation absorbing mask 120 are wider than the projection of the distal end of the anti-scatter plate 80. Preferably, the Z-direction strips 122 are generously wide to compensate for any allowed tolerance, vibrational motion, and cumulative alignment stack-up errors leading to mispositioning of anti-scatter plates 80 that could cast shadows on crystals 110 of array 108. Preferably, the Z-direction strips 122 of the radiation absorbing mask 120 are sufficient to absorb 90% or more of the x-rays that are incident on it.

Preferably, the radiation absorbing mask 120 is a high-density absorber and constructed of a material with a high atomic number that is highly absorbing for radiation produced by the x-ray source 14, such as tungsten or any other material that may be etched or manufactured in another precise way. The masks can be stacked to provide 0.5-2 mm thickness to increase the radiation attenuation. Typically, the tungsten sheets are available in 0.125 mm thick sheets. Consequently, three or four 0.125 mm thick radiation absorbing masks 120 are preferred for attenuating the x-ray beam. Thicker masks do not need to be stacked and can be made by other suitable methods.

With continuing reference to FIG. 10A, apertures 126 in the radiation absorbing masks 120 are photochemically etched and accurately and repetitiously controlled. Typically, the spatial resolution of the scanner is chosen by the width of the crystal 110 of the array 108 and is controlled by the size of the aperture or the solid angle of radiation that can measured by radiation detector assembly 30. The spatial resolution is controlled by the radiation absorbing mask 120 that is a precise part providing accurate apertures 126 that determine the spatial resolution. Further, the scintillation crystals 110 in large arrays tend to have a lack of precise uniformity in the surface area that is exposed to x-ray radiation, due to the cutting or etching tolerances, uneven reflective coating layers, or the like. The use of the grid that defines apertures 126 precisely fixes the cross section of the radiation beam that each scintillation crystal 110 receives and causes each to have exact same sampling window. Alternatively, the sampling window and the apertures can have a precisely controlled non-uniform size to provide different resolution across a detector module. Analogously, the aperture sizes can change from detector module to detector module to provide non-uniform resolution across the detector assembly.

The apertures 126 are precisely referenced to alignment openings 128 in the same grid and are made to high tolerances as afforded by the photochemical etching process or other precise methods of manufacturing.

With continuing reference to FIG. 10A, the radiation absorbing masks 120 are preferably configured to include thin bridges or circumferential strips 130, which provide mechanical stability by reducing the free aperture length. Preferably, strips 130 are comparable with the width of an intra-element gap between detector elements running in a circumferential direction.

With continuing reference to FIG. 10A and further reference to FIG. 10B, the radiation absorbing masks 120 are constructed to have an interleaving edges geometry to prevent the radiation from passing through a gap between any two individual masks. Each edge of the radiation absorbing mask 120 along its width is etched or cut approximately half way, creating a stepped edge 134. Steps on opposite sides of the mask are provided on the opposite surfaces of the mask to permit alternate stacking of the radiation absorbing masks 120 across the length of the radiation detector assembly 30 without inter-module gaps. Alternately, the stepped edges can be etched or cut into the same surface for simplicity of manufacture. Alternate masks are turned over to engage their neighbors.

With reference again to FIGS. 7, 9 and 10A, alignment pins 160 of each anti-scatter module 78 precisely mate with the precision openings 128 of radiation absorbing mask 120 and precision alignment openings 162 of the corresponding detector subassembly module 100 to provide alignment of the scintillator crystal array 108 with the mask 120 and the vanes 80 of the anti-scatter module 78. Because both the alignment openings 162 and the pins 160 are defined with precision, the parts are precisely aligned upon insertion. No adjustment in the alignment is necessary. As best seen in FIG. 7, several radiation absorbing masks 120 can be stacked on the pins 160 without any loss of accuracy.

The alignment of the scintillator crystal array 108 to the anti-scatter module 78 arranges the scintillation crystals 110 in the gaps between the anti-scatter plates 80 as best seen in FIGS. 8 and 11. The radiation absorbing mask 120 is arranged between the anti-scatter plates 80 and the scintillation crystals 110. The scintillation crystals 110 view the x-ray source through the grid apertures 126 and between the anti-scatter plates 80, such that the radiation, which does not angularly deviate from the unscattered radiation, reaches the individual elements of the detector array 104.

With reference to FIG. 12, the radiation absorbing mask 120 made by one of the alternative methods of manufacturing the radiation absorbing mask is depicted. Slots or grooves 164 are provided in a matrix 166 of a low radiation absorbing material such as BeAl Alloy, plastics, epoxy resin, or any other material that is relatively transparent to the x-ray radiation. A tungsten powder or any other high atomic powder material is then deposited by casting or injection molding in the provided slots and grooves. Yet the radiation absorbing mask might be made by using ECOMASS™ high atomic number powder materials in a plastic matrix available from PolyOne Corp. These materials can be formed in different shapes by standard manufacturing techniques such as extrusion. The radiation absorbing mask might be fabricated by a use of a very precise tooling.

With continuing reference to FIGS. 1-12 and with further reference to FIG. 13, a preferred method 170 for assembling the radiation detector assembly 30 is described.

In a step 172, the anti-scatter modules 78 are aligned with the alignment openings 70 by coupling the alignment pins 86 with the alignment openings 70 of the alignment plates 60. In a step 174, radiation absorbing masks 120 are stacked on the pins 160 of the anti-scatter modules 78. In a step 176, each detector subassembly module 100 is mounted to each corresponding fixed anti-scatter module 78 using the mating alignment pins 160 and openings 162.

Although the radiation detector assembly 30 has been described with reference to a computed tomography imaging scanner, it is readily modified for use in other imaging systems. For example, a gamma camera for nuclear medical imaging typically includes detector arrays substantially similar to the photodetector array 104 with scintillators suitable for converting radiation produced by an administered radiopharmaceutical to light detectable by the detector array. Analogously, these techniques can be applied to conventional x-ray, digital x-ray, fluoroscopy, and the like.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A two-dimensional radiation detector for a radiographic scanner, the radiation detector comprising:
    an anti-scatter module;
    a first aligning means for aligning the anti-scatter module with a spatial focus;
    a second aligning means for aligning the anti-scatter module;
    a detector subassembly module, each detector subassembly module including a substrate and an array of detector elements arranged on the substrate to detect radiation, and
    a radiation absorbing mask formed as a grid and arranged between the array of the detector elements and the anti-scatter module; wherein the second aligning means includes alignment pins that align the anti-scatter module with the detector subassembly module
    wherein the second aligning means further includes:
    alignment openings disposed on the substrate; and
    alignment openings disposed on the radiation absorbing mask; wherein
    the alignment pins are disposed on the anti-scatter module, such that inserting the pins into the radiation absorbing mask alignment openings and the substrate alignment openings aligns the detector element array with the radiation absorbing mask and the anti-scatter module.

2. The radiation detector as set forth in claim 1, wherein the radiation absorbing mask is formed of a radiation absorbing material.

3. The radiation detector as set forth in claim 1, further including:
    one or more of additional radiation absorbing masks stacked on the alignment pins.

4. The radiation detector as set forth in claim 3, wherein the radiation absorbing mask has stepped edges, which interleave with stepped edges of adjacent radiation absorbing masks.

5. The radiation detector as set forth in claim 1, wherein the anti-scatter module includes:
    a plurality of anti-scatter vanes formed of a material which is substantially absorbing for radiation produced by the radiographic scanner.

6. The radiation detector as set forth in claim 5, wherein the radiation absorbing mask includes:
    first strips parallel to the plurality of anti-scatter vanes, which first strips are wider than a thickness of the anti-scatter vanes and are equal or greater than a gap between the detector elements of the array.

7. The radiation detector as set forth in claim 5, wherein the radiation absorbing mask includes:
    second strips perpendicular to the plurality of anti-scatter vanes, which second strips are of substantially a same dimension as a gap between the detector elements.

8. The radiation detector as set forth in claim 5, wherein the radiation absorbing mask has stepped edges, which interleave with stepped edges of adjacent radiation absorbing masks.

9. The radiation detector as set forth in claim 1, wherein the radiation absorbing mask defines precise apertures, which align with and set a resolution of the elements of the detector array.

10. The radiation detector as set forth in claim 9, wherein the apertures are precisely defined by photochemical etching.

11. The radiation detector as set forth in claim 1, wherein the detector element array includes:
    a scintillation array that produce scintillation events responsive to radiation produced by the radiographic scanner, wherein the scintillation array includes scintillation elements; and
    a photodetector element array, each photodetector element of the array being arranged to view one of the scintillation elements of the scintillation array to convert light from the scintillation events into electrical signals.

12. The radiation detector as set forth in claim 11, wherein the scintillation element array is arranged in a two-dimensional rectangular array with a rectangular array of interfaces between adjoining scintillation elements and the radiation absorbing mask includes:

a rectangular array of strips of a radiation absorbent material that defines the grid, the strips overlying interfaces between adjacent scintillation elements.

13. The radiation detector as set forth in claim 1, wherein the radiation absorbing mask includes:

a first plurality of strips extending along a first direction; and a second plurality of strips extending along a second different direction.

14. A two-dimensional radiation detector for a radiographic scanner, the radiation detector comprising:

an anti-scatter module;

a first aligning means for aligning the anti-scatter module with a spatial focus;

a second aligning means for aligning the anti-scatter module;

a detector subassembly module, each detector subassembly module including a substrate and an array of detector elements arranged on the substrate to detect radiation, and a radiation absorbing mask formed as a grid and arranged between the array of the detector elements and the anti-scatter module; wherein the second aligning means includes alignment pins that align the anti-scatter module with the detector subassembly module wherein the radiation absorbing mask includes first alignment openings and the detector subassembly module includes second alignment openings, and the alignment pins extend through the first alignment openings of the radiation absorbing mask and the second alignment openings of the detector subassembly module.

15. The radiation detector as set forth in claim 14, wherein the first direction is perpendicular to the second direction.

16. A radiation detector of a radiographic scanner, the radiation detector includes a plurality of detector modules, each detector module including:

an anti-scatter module, including a plurality of vanes and alignment pins; and a rectangular grid including:

a plurality of wider strips, arranged parallel to each other, each wider strip being wider than a width of each vane, a plurality of thinner strips, the plurality of thinner strips being arranged perpendicular to the wider strips to form uniform openings, each wider strip is aligned with a corresponding vane.

17. The radiation detector as set forth in claim 16, further including:

a detector array including a plurality of detector elements arranged to form a multi-dimensional rectangular array, each two adjoining detector elements of the array being separated by interfaces, the interfaces are aligned with the rectangular grid to place the grid openings between the vanes and the detector elements of the array to define resolution of the radiographic scanner, wherein the detector array includes a substrate with alignment openings, and the alignment pins of the anti-scatter module lie within and extend through the alignment openings in the substrate of the detector array.

18. A computed tomography scanner including:

an x-ray source mounted to rotate about an examination region, the x-ray source emitting a cone shaped x-ray beam from a radiation focal point and traversing the examination region;

a two-dimensional radiation detector which receives the cone beam of radiation that has traversed the examination region, the radiation detector including a plurality of detector modules, each detector module including:

an anti-scatter module, which includes alignment pins, a detector subassembly module aligned with the anti-scatter module, each detector subassembly module including a substrate and an array of detector elements arranged on the substrate to detect radiation, and a radiation absorbing mask formed as a grid, the mask being arranged between and aligned with the array of the detector elements and the anti-scatter module, wherein the alignment pins of the anti-scatter module extend through alignment openings in the mask and alignment openings in the detector subassembly module; and a reconstruction processor for reconstructing signals from the detector element array into a volumetric image.

19. A method for manufacturing a radiation detector for a computed tomography scanner, the method comprising:

aligning an anti-scatter module, which includes extending alignment pins, with: a detector subassembly module including a substrate and an array of detector elements arranged on the substrate to detect radiation, and a radiation absorbing mask disposed between the anti-scatter module and the detector elements of the array; and inserting the alignment pins through alignment openings in the mask and alignment openings in the detector subassembly module.

20. The method as set forth in claim 19, further including:

forming a radiation absorbing mask by photoetching a radiation opaque material to define a grid.

21. The method as set forth in claim 19, wherein the scanner includes an x-ray source on a rotating gantry that produces a cone of x-rays, which pass through an examination region and strike the radiation detector, the method further including:

mounting the anti-scatter module onto the computed tomography scanner, with a spatial focal point of the anti-scatter module being aligned with a focal point of the x-ray source prior to inserting the pins into the alignment openings of the mask and the detector subassembly module.

22. The method as set forth in claim 19, wherein as the pins are inserted in the alignment openings of the radiation absorbing mask, edges of adjacent radiation absorbing masks are interleaved.

23. The method as set forth in claim 19, further including:

defining uniform apertures in the radiation absorbing mask to precisely fix an amount of radiation received by each detector element of the array.

* * * * *